(12) United States Patent
Ju et al.

(10) Patent No.: US 6,320,660 B1
(45) Date of Patent: Nov. 20, 2001

(54) SIEVING APPARATUS FOR A BIO-CHIP

(75) Inventors: Jau-Jiu Ju, Hsinchu Hsien; Der-Ray Huang, Kuang-Ming Hsin Tsun; Tzu-Ping Yang, Taipei, all of (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 09/545,954

(22) Filed: Apr. 10, 2000

(30) Foreign Application Priority Data

Mar. 24, 2000 (TW) ................................................. 89105441

(51) Int. Cl.$^7$ ................................................. G01N 21/25
(52) U.S. Cl. ..................... 356/417; 356/317; 356/318; 356/344; 250/458.1; 250/459.1
(58) Field of Search ..................... 356/341, 300, 356/303, 307, 311, 301, 317, 318, 417; 250/458.1, 459.1, 469.1, 461.2

(56) References Cited

U.S. PATENT DOCUMENTS

| | | | |
|---|---|---|---|
| 5,166,813 | * 11/1992 | Metz | 359/15 |
| 6,159,681 | * 12/2000 | Zebala | 435/4 |
| 6,205,354 | * 3/2001 | Gellermann et al. | 356/301 |

* cited by examiner

*Primary Examiner*—Fannie L. Evans
*Assistant Examiner*—Roy M. Punnoose
(74) *Attorney, Agent, or Firm*—Jiawei Huang; J.C. Patents

(57) ABSTRACT

The invention is directed to a sieving apparatus for a bio-chip, which has a light source, a HOE unit, a splitter, an objective lens, a filter, and an optical signal sensor. The HOE unit is coupled with a light source, so as to diffract the light into a zeroth order beam and a first order beam. The zeroth order beam has no deflection but the first order beam has a deflection from the zeroth order beam. The splitter is coupled to the HOE unit, so as to lead the two beams to the objective lens, which further leads the two beams to the bio-chip, in which the first order beam is incident onto the bio-chip from an incident angle, causing a florescent light from the sample. The bio-chip also reflects the zeroth order beam. Both the reflected zeroth order beam and the fluorescent light travel through the objective lens and the splitter. The filter is coupled to the splitter, so that an undesired portion of the light beams incident on the splitter is filtered. The optical sensor receives the light beams after the filter. The zeroth order beam is used to generate a focusing signal and a tracking signal. The focussing signal and the tracking signal are used to control the servo, so as to align the optical sensor to the samples for detecting the florescent light. Alternatively, the sensor can be fixed but the bio-chip is shifted by the servo system.

22 Claims, 5 Drawing Sheets

SIEVING APPARATUS FOR A BIO-CHIP

CROSS-REFERENCE TO RELATED APPLICATION

This application claims the priority benefit of Taiwan application Ser. No. 89105441, filed Mar. 24, 2000.

BACKGROUND OF THE INVENTION

1. Field of Invention

The present invention relates to an optical inspection system. More particularly, the present invention relates to a sieving apparatus for sample on a bio-chip.

2. Description of Related Art

A bio-chip is widely used in a biologic inspection system to sieve out the interesting samples. Usually, one sample or various samples are put on a bio-chip at the detection units, respectively. The detection units on the bio-chip are sieved one by one. The bio-chip is implemented into a detection system for sieving each sample. The detection system is an optical detection system. The sample is illuminated by a light beam generated from a light source. The optical detection system then detects a fluorescent light from the sample on the bio-chip, whereby a particular component content in the sample is detected. As a result, the samples having the particular component are sieved out from the samples pool.

The bio-chip typically includes a specified material at the detection units. Once the samples are put onto the bio-chip, the material reacts with the particular component contained if the detected sample contain the particular component. After reaction, the component becomes fluorescent if the reacted component is illuminated by a light with a specific wavelength. Currently, the bio-chip detection apparatus needs an external light source. The external light source emits a light beam that is incident onto the detection unit of the bio-chip from side. If the fluorescent signal is successfully detected out, the sample is indicated as the sample containing the particular component.

FIG. 1 is a drawing, schematically illustrating a conventional optical detection system for a bio-chip. In FIG. 1, the conventional optical detection system includes an objective lens 100, a slit 102, a filter 104, a photomultiplier tube 106, an electronic filter 108, and a computer 110.

A bio-chip 130 with the sample is illuminated by an argon ion laser beam 150 from side with an incident angle of 45 degrees through a lens 140. The laser beam illuminated the specified sample of the bio-chip 130, then the sample containing the component produces a fluorescent light 120. The fluorescent light 120 goes through the objective lens 100, the slit 102, the filter 104, and then reach the photomultiplier tube 106. The photomultiplier tube 106 amplifies the fluorescent light 120 and convert it into an electronic signal. The electronic signal is exported to the electronic filter 108, and then to the computer 110 for processing.

In the foregoing conventional optical detection system for the bio-chip have to associate with an external light source. The whole system is complex and has a large volume. It is difficult to align and adjust. In this manner, the detection system for bio-chip is installed on a fixed frame only at a medical center or the similar centers. The sample sieving process is always performed at the centers. This causes very inconvenient and inefficient particularly when a large amount of samples need to be sieved.

SUMMARY OF THE INVENTION

The invention provides a sieving apparatus for a bio-chip. The sieving apparatus integrates the light source and the detecting part in a single apparatus. Since the sieving apparatus is well compacted, the sieving apparatus is portable and can efficiently process sieve for a large amount of samples. The sieving apparatus of the invention includes a holographic optical element (HOE), which allows a light beam to illuminate the sample of the bio-chip from side with a specific incident angle. The bio-chip can efficiently absorb the illuminating light and generate more fluorescent effect. The sieving efficiency is effectively improved. This is particularly helpful for processing a large amount of samples. Furthermore, the sieving apparatus can be easily aligned and adjusted for detecting the fluorescent signals. Further still, the reflection light from the bio-chip is used to automatically locate the detection point at the samples through a servo system. The sieving efficiency is further greatly improved. As a result, a large amount of samples can be efficiently sieved.

As embodied and broadly described herein, the invention provides a sieving apparatus for a bio-chip, which includes a light source, a HOE unit, a splitter, an objective lens, a filter, and an optical signal sensor. The HOE unit is coupled with a light source, so as to diffract the light into a zeroth order beam and a first order beam. The zeroth order beam has no deflection but the first order beam has a deflection from the zeroth order beam. The splitter is also coupled to the HOE unit, so as to lead the zeroth order beam and the first order beam to the objective lens. The objective lens further leads the two light beams to the bio-chip, in which the first order beam is incident onto the bio-chip from a specific incident angle, causing a florescent light from the sample. The bio-chip also reflects the zeroth order beam. Both the reflected zeroth order beam and the fluorescent light travel through the objective lens and the splitter. The filter is coupled to the splitter, so that the undesired portion of the light beams incident on the splitter is filtered by the filter. The optical sensor receives the light beams after the filter. The zeroth order beam is used to generate a focusing signal and a tracking signal. The focussing signal and the tracking signal are used to control the servo, so as to align the optical sensor to the samples for detecting the florescent light. The samples therefore are sieved to see whether the sample contains a particular component or not.

The invention provides another sieving apparatus for a bio-chip, which includes a light source, an HOE unit, a first splitter, a second splitter, an objective lens, a filter, a servo signal generating system, and a signal sensor. The HOE unit is coupled with a light source, so as to diffract the light source into a zeroth order beam and a first order beam. The zeroth order beam has no deflection, but the first order beam has a deflection from the zeroth order beam. The first splitter is coupled to the HOE unit, so as to lead the zeroth order beam and the first order beam to the objective lens. The two light beams then is led to the bio-chip through the objective lens. The first order beam is refracted by the objective lens, so that the first order beam is incident onto the sample of the bio-chip by a specific incident angle. If the sample contains the particular component, a fluorescent light is emitted from the sample. The bio-chip also reflects the zeroth order beam, which together with the fluorescent light travel back through the objective lens and reach the first splitter. The second splitter, which is coupled to the first splitter, then splits the two beams. A portion of the beams after the second splitter is led to the servo signal generating system, which is coupled to second splitter. The servo signal generating system accordingly generates a focusing signal and a tracking signal, which are used to control a shift of the bio-chip to a desired location. The beams passes through the second splitter is further filtered by the filter, and then is sensed by a signal sensor, so as to detecting the florescent light. The fluorescent light is generated by the sample contain the particular component. In this manner, the samples are sieved.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Theory of the bio-chip for sieving samples is that the particular component of the sample has a chemical react with a material that is formed on a bio-chip at a detection unit. The detection unit can have one sample or various samples. The component after reaction absorbs light and becomes fluorescent when the component is illuminated by a light with a specific wavelength. For example, when a green light, such as a green laser light, with a wavelength of about 532 nm is incident onto the reacted component, a fluorescent light with a wavelength of about 540 nm is emitted. A sieving apparatus of bio-chip can detect the fluorescent light with the specific wavelength, so as to sieve the sample. Generally, the operation mechanism is similar to the operation mechanism used in an optical disc for accessing data.

First Embodiment

Figure 1:
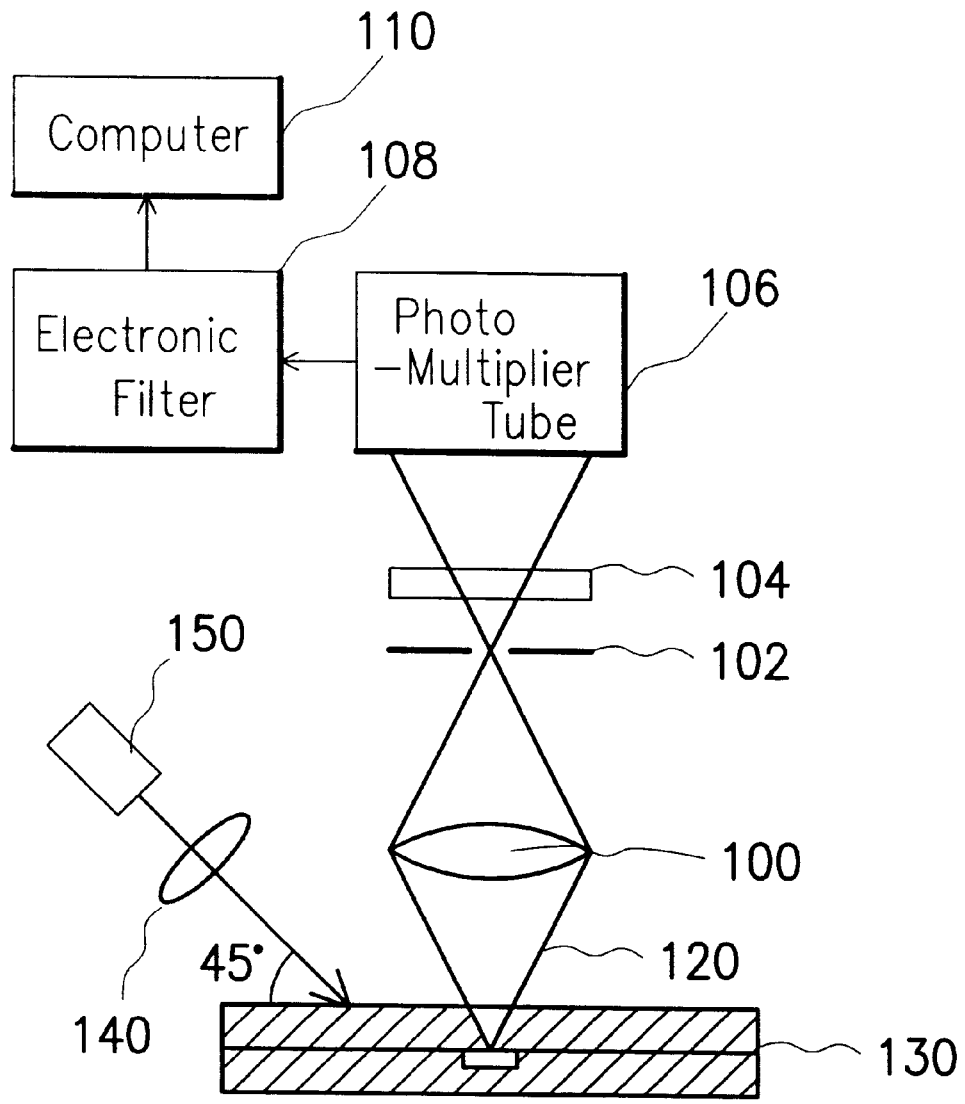
FIG. 1 is a drawing, schematically illustrating a conventional optical detection system for a bio-chip.
Figure 2A:
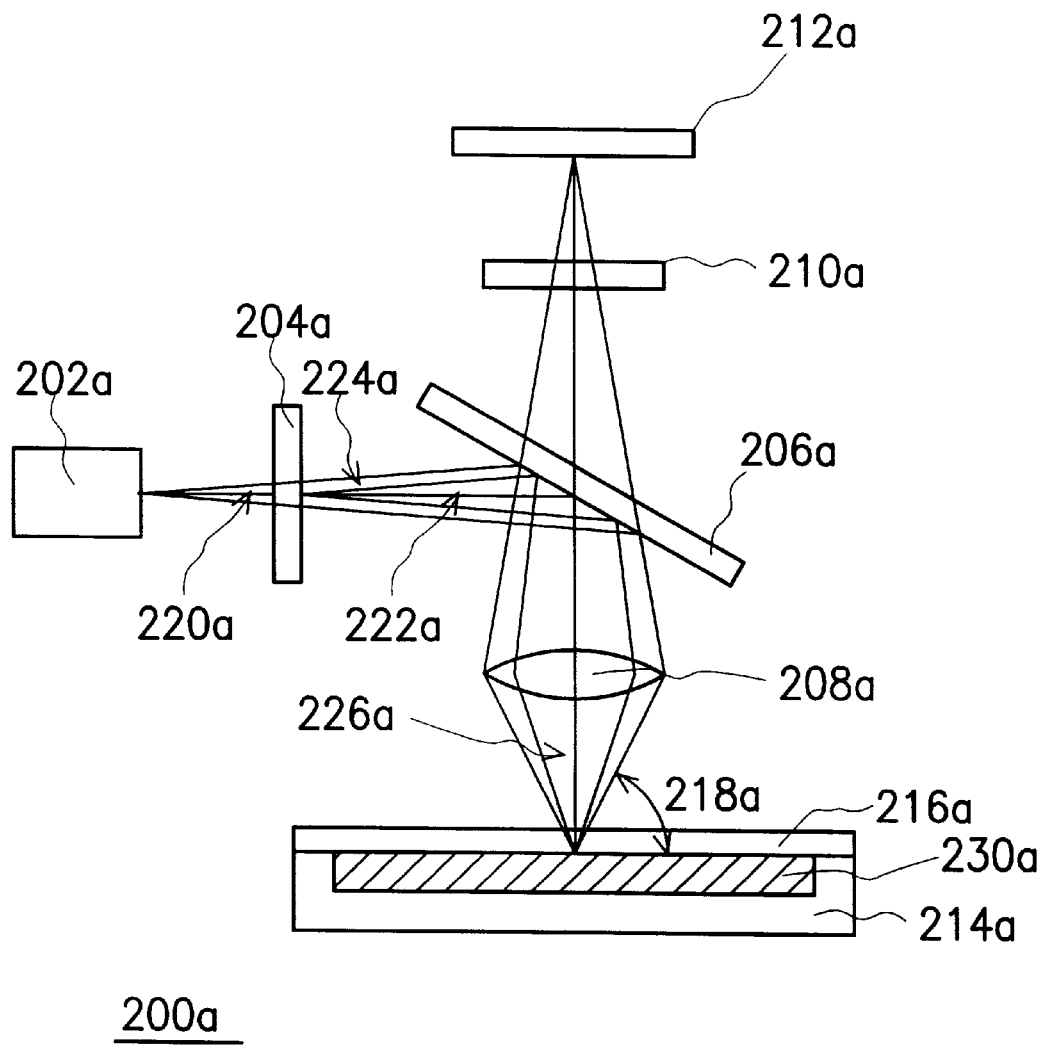
FIG. 2A is a drawing, schematically illustrating an optical detection system for bio-chip, according to the first preferred embodiment of the invention.

FIG. 2A is a drawing, schematically illustrating an optical detection system for bio-chip, according to the first preferred embodiment of the invention. In FIG. 2A, an optical sieving apparatus 200a is also an optical detection system. The optical detection system includes a light source 202a, an HOE unit 204a, a beam splitter 206a, an objective lens 208a, a filter 210a, and a signal sensor 212a. A bio-chip 230a is held by a holder 214a. Location of the holder 214a can be adjusted by a mechanical unit (not shown), such as a servo system. A cover glass 216a covers the bio-chip 230a for protection from contamination. The cover glass, for example, is about 0.1–1.2 mm.

In the sieving apparatus 200a, the light source 202a, such as a laser light source, is used to produce light to illuminate the bio-chip 230a. Wavelength of the light source can be about 400 nm–600 nm. The HOE unit 204a is coupled to the light source 202a for receiving the light beam 220a from the light source 202a. The HOE unit 204a then diffracts the light beam 220a to form a zeroth order beam 222a and a first order beam 224a. Due to the optical properties, the zeroth order beam has no deflection and travels on the optical path, but the first order beam has a deflection from the zeroth order beam. This phenomenon is a natural physical property for the HOE unit 204a.

The beam splitter 206a is coupled to the HOE unit 204a for receiving the zeroth order beams 222a and the first order beam 224a. Generally, the HOE unit 204a is located between the light source 202a and the beam splitter 206a. The zeroth order beam 222a and the first order beam 224a are deflected by the beam splitter 206a onto the bio-chip at the detection unit that has the sample to be sieved. Between the beam splitter 206a and the bio-chip 230a, the objective lens 208a is used to focus the zeroth order beam 222a and the first order beam 224a onto the desired sample on the bio-chip 230a. Due to the geometric design of the objective lens 208a, the first order beam is incident onto the sample by a specific incident angle 218a from side. The bio-chip 230a is properly shifted by the servo system, so as to scan all the samples for sieve. In this manner, the sample illuminated by the light from side has a better fluorescent efficiency. The incident angle 218a can range about 30–50 degrees. Preferably, the incident angle 218a is about 45 degrees. The numerical aperture (NA) of the objective lens 208a is about 0.4–0.6. The structure of the objective lens 208a can be, for example, a spherical lens, a rod lens, or similar lens, in which the rod lens can produce an elliptic light spot and has greater advantages for scanning the samples.

The filter 210a and the signal sensor 212a are located on the optical path at one side of the beam splitter 206a opposite to the side having the objective lens 208a and the bio-chip 230a. The filter 210a is coupled between the signal sensor 212a and the beam splitter 206a. The filter 210a filters undesired light in wavelength and allows the fluorescent light to pass and reach the signal sensor 212a to determine whether there is the desired fluorescent light. The signal sensor 212a includes photodetector to detect the fluorescent light.

Still referring to FIG. 2A, the light beam 220a from the light source 202a is diffracted by the HOE unit 204a into the zeroth order beam 222a and the first order beam 224a. The beam splitter 206a leads the beams 222a and 224a onto the objective lens 208a, and then onto the bio-chip 230a. The zeroth order beam 222a does not deflect from the optical axis but the first order beam deflects from the optical axis, surrounding the zeroth order beam. The first order beam 224a is refracted by the objective lens 208a and therefore is incident on the sample of the bio-chip 230a by the incident angle 218a. If the sample contains the detected component, the fluorescent light 226a is produced. The fluorescent light 226a travels back to the signal sensor 212a through the objective lens 208a, the beam splitter 206a, and the filter 210a. The zeroth order beam is reflected to an optical signal sensor for generating a tracking signal and focusing signal, used to control the servo system to move the bio-chip 230a.

Figure 3:
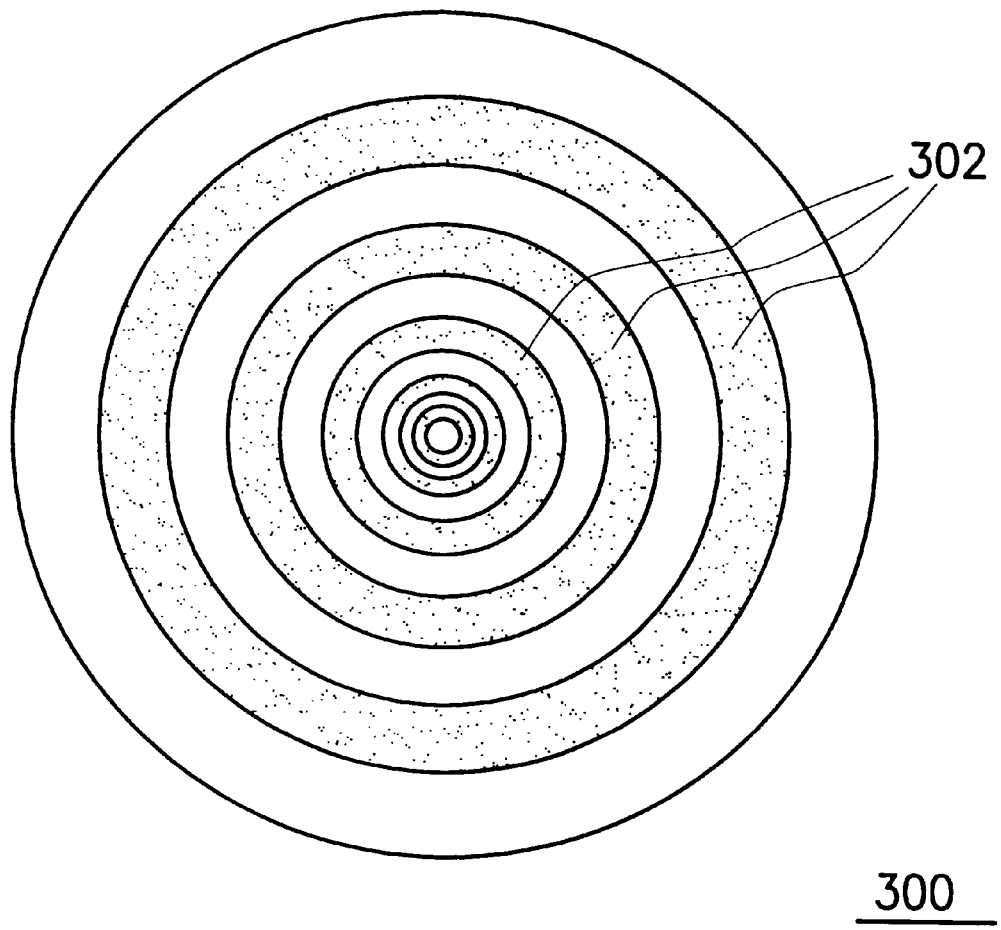
FIG. 3 is a drawing, schematically illustrating a circular HOE unit used in the optical detection system for bio-chip, according to the first preferred embodiment of the invention.

The HOE unit 204a can be a circular HOE unit. FIG. 3 is a drawing, schematically illustrating a circular HOE unit used in the optical detection system for bio-chip, according to the first preferred embodiment of the invention. In FIG. 3, the circular HOE unit 300 has several circular strips 302, which are concentric and are gradually wider toward the circular periphery, in which the pitches between the strips are also gradually wider. The density of the strips near to the center is higher than the density near to the edge.

Figure 2B:
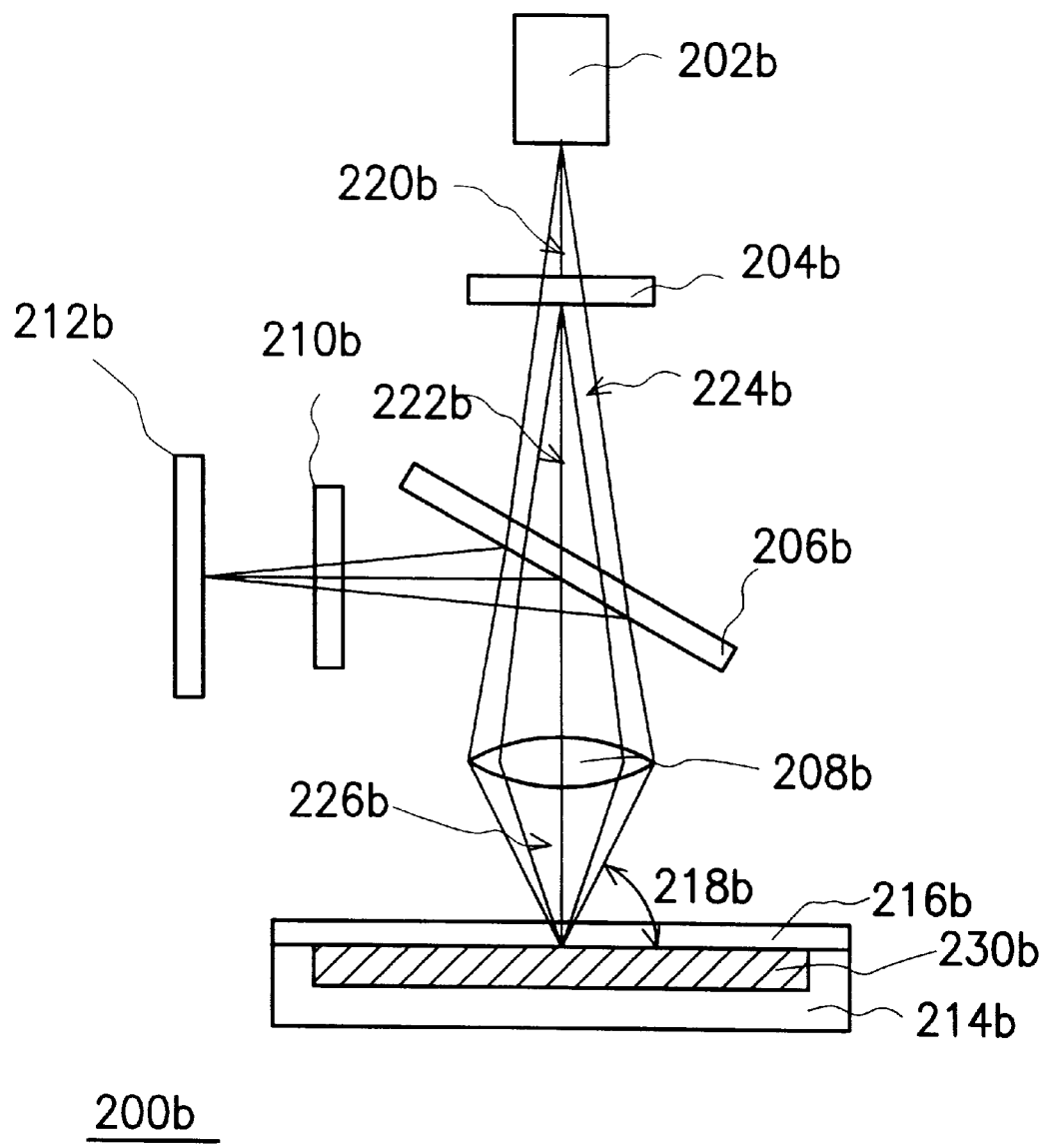
FIG. 2B is a drawing, schematically illustrating another optical detection system for bio-chip, according to the first preferred embodiment of the invention.

Similarly, FIG. 2B is a drawing, schematically illustrating another optical detection system for bio-chip, according to the first preferred embodiment of the invention. In FIG. 2B, the sieving apparatus of bio-chip 200b is similar to the one in FIG. 2A but has a different arrangement of locations for the beam signal sensor and the light source. The bio-chip 200b includes a light source 202b, an HOE unit 204b, a beam splitter 206b, an objective lens 208b, a filter 210b, and a signal sensor 212b. A bio-chip 230b is held by a holder 214b. Location of the holder 214b can be adjusted by a mechanical unit (not shown), such as a servo system. A cover glass 216b covers the bio-chip 230b for protection from contamination. The cover glass, for example, is about 0.1–1.2 mm.

In the sieving apparatus 200b, the light source 202b, such as a laser light source, is used to produce light to illuminate the bio-chip 230b. Wavelength of the light source can be about 400 nm–600 nm. The HOE unit 204b is coupled to the light source 202b for receiving the light beam 220b from the light source 202b. The HOE unit 204b then diffracts the light beam 220b to form a zeroth order beam 222b and a first order beam 224b. Due to the optical properties, the zeroth order beam has no deflection and travels on the optical path, but the first order beam 224b has a deflection from the zeroth order beam 222b.

The beam splitter 206b is coupled to the HOE unit 204b for receiving the zeroth order beams 222b and the first order beam 224b. The HOE unit 204b is located between the light source 202b and the beam splitter 206b. The zeroth order beam 222b and the first order beam 224b travel through the beam splitter 206b, and reach the bio-chip 230b. Between the beam splitter 206b and the bio-chip 230b, the objective lens 208b is used to focus the zeroth order beam 222b and the first order beam 224b onto the desired sample on the bio-chip 230a. Due to the geometric design of the objective lens 208b, the first order beam is incident onto the sample by a specific incident angle 218b from side. The bio-chip 230b is properly shifted by the servo system, so as to scan all the samples for sieve. In this manner, the sample illuminated by the light from side has a better fluorescent efficiency. The incident angle 218b can range about 30–50 degrees. Preferably, the incident angle 218b is about 45 degrees. The NA of the objective lens 208b is about 0.4–0.6. The structure of the objective lens 208b can be, for example, a spherical lens, a rod lens, or similar lens, in which the rod lens can produce an elliptic light spot and has greater advantages for scanning the samples.

Still referring to FIG. 2B, the filter 210b and the signal sensor 212b are located on an optical path vertical to the optical path between the light source 202b and the bio-chip 230b. The filter 210b is coupled between the signal sensor 212b and the beam splitter 206b. As the zeroth order beam 222b and the first order beam 224b travel through the beam splitter 206b and the objective lens 208b, and reach the bio-chip 230b, the sample is illuminated by the first order beam 224b from side at the incident angle 218b. The sample therefore produces a fluorescent light 226b if the sample contains the component to be detected. The fluorescent light 226b travels along the optical path back to the beam splitter 206b through the objective lens 208b. The beam splitter 206b deflects the fluorescent light 226b into the filter 210b.

The filter 210b typically filters undesired light in wavelength about other than the fluorescent light. The fluorescent light 226b passes the filter 210b and reaches the signal sensor 212b to indicate the component contained in the sample. The signal sensor 212a includes photodetector to detect the fluorescent light. The zeroth order beam 222b may also be reflected by the bio-chip 230b to an optical signal sensor to generate a tracking signal and a focusing signal, used for control the servo system to move the bio-chip 230b.

The HOE unit 204b can be a circular HOE unit as shown in FIG. 3. The circular HOE unit 300 has several circular strips 302, which are concentric and are gradually wider toward the circular periphery, in which the pitches between the strips are also gradually wider. The density of the strips near to the center is higher than the density near to the edge.

Second Embodiment

Figure 4:
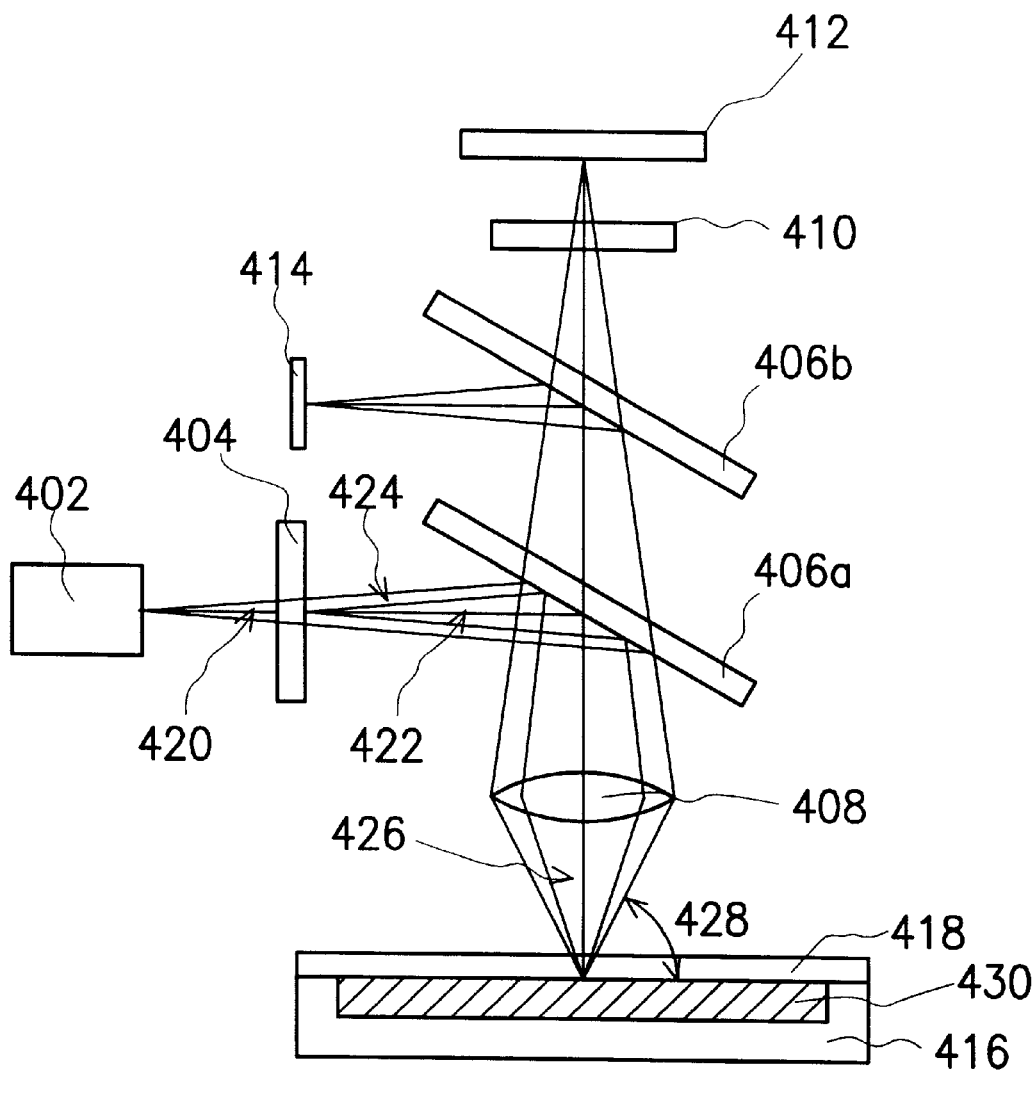
FIG. 4 is a drawing, schematically illustrating an optical detection system for bio-chip, according to the second preferred embodiment of the invention.

FIG. 4 is a drawing, schematically illustrating an optical detection system for bio-chip, according to a second preferred embodiment of the invention. In FIG. 4, a sieving apparatus for bio-chip 400 includes a light source 402, an HOE unit 404, a first beam splitter 406a, a second beam splitter 406b, an objective lens 408, and filter 410, a servo signal sensor 414, and a signal sensor 412.

Similar to the first embodiment, a bio-chip 430 is held by a holder 416. Location of the holder 416 can be adjusted by a mechanical unit (not shown), such as a servo system. A cover glass 418 covers the bio-chip 430 for protection from contamination. The cover glass 418, for example, is about 0.1–1.2 mm.

In FIG. 4, the light source 402, such as a laser light source, is used to produce light to illuminate the bio-chip 430. Wavelength of the light source can be about 400 nm–600 nm. The HOE unit 404 is coupled to the light source 402 for receiving the light beam 420 from the light source 402. The HOE unit 204a, such as a circular HOE, then diffracts the light beam 420 to form a zeroth order beam 422 and a first order beam 424. Due to the optical properties, the zeroth order beam 422 has no deflection and travels on the optical path, but the first order beam 424 has a deflection from the zeroth order beam 422.

The first beam splitter 406a is coupled to the HOE unit 404 and is located on one side of the HOE unit 404 opposite to the light source 402. The zeroth order beam 422 and the first order beam 424 are deflected by the first beam splitter 406a. The objective lens 408 is coupled to the first beam splitter 406a, so as to receive the zeroth order beam 422 and the first order beam 424 from the first beam splitter 406a. The objective lens 408 focuses the zeroth order and the first order beams onto the sample at the bio-chip 430. The objective lens 408 also refracts the first order beam 424, whereby the first order beam 424 is incident on the sample by an incident angle 428 to generate the fluorescent ling 426. The incident angle 428 can range from about 30 degrees to about 50 degrees, in which 45 degrees is preferred. The NA of the objective lens 408 is about 04–06. The structure of the objective lens 408 can be, for example, a spherical lens, a rod lens, or similar lens, in which the rod lens can produce an elliptic light spot and has greater advantages for scanning the samples.

In FIG. 4, the second beam splitter 406b is coupled to the first beam splitter 406a at the side opposite to the bio-chip 430. The fluorescent light 426 together with the zeroth order beam 422 reflected by the bio-chip 430 travel along the optical path through the objective lens 408, the first beam splitter 406a, and reach the second beam splitter 406b. A portion of the zeroth order beam 433 and the fluorescent light 426 is deflected by second beam splitter 406b onto the servo signal sensor 414. The servo signal sensor 414 can generated the tracking signal and the focusing signal to control the servo system to move the bio-chip 430. The rest portion of the zeroth order beam 422 and the fluorescent light 426 continuously travel through the filter 410 and reaches the signal sensor 412. Since the filter 410 can filter away the light in wavelength about other than the wavelength of the fluorescent light 426, only the fluorescent light 426 can reach the signal sensor 412. The photodetector of the signal sensor 412 detects the fluorescent light to indicate whether the sample contain the component or not.

In the foregoing, the light beam 420 emitted from the light source 402 reaches the bio-chip 430 through the HOE unit 404, the first beam splitter 406a, and the objective lens 408. The HOE unit 404 diffracts the light beam 420 to be the zeroth order beam 422 and the first order beam 424. The first beam splitter 406a deflects the beams onto the bio-chip 430 through the objective lens 408. Since the effects from the HOE unit 404 and the objective lens 408, the first order beam can be incident on the sample by the specific incident angle 428, so as to illuminate the sample. If the sample contains the component, the fluorescent light is generated and is detected by the signal sensor 412. A portion of the zeroth order beam is deflected by the second beam splitter 406b onto the servo signal sensor 414, whereby the tracking signal and the focusing signal are generated for use to control the servo system. All samples on the bio-chip can be automatically and efficiently scaned.

Like the arrangement between FIG. 2A and FIG. 2B, the light source 402 and the signal sensor 412 in FIG. 4 can be rearranged at the different optical path.

In conclusion, the sieving apparatus for bio-chip of the present invention integrates the light source and the sensing part into one single body. The system is greatly simplified, and the volume is also greatly reduced. This allows the sieving apparatus to be portable. In order to integrate the light source and the sensing part, an operation mechanism associate the HOE unit like the operation mechanism for optical pickup head is employed. As a result, the detection light spot can be automatically aligned to the samples. The samples on the bio-chip can be efficiently scanned and sieved.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A sieving apparatus for a bio-chip, which has at least one sample to be sieved, the apparatus comprising:

a light source to emit a light beam;

a holographic optical element (HOE) unit, used to receive the light beam from the light source and diffract the light beam to form a zeroth order beam and a first order beam, wherein the zeroth order beam remains on an optical path without deflection, and the first order beam is deflected away the optical axis abutting the zeroth order beam;

a beam splitter, receiving the zeroth order beam and the first order beam from the HOE unit;

an objective lens associating with the beam splitter, wherein the beam splitter also leads the zeroth order beam and the first order beam to the objective lens, and the objective lens refracts the zeroth order beam and the first order beam to the bio-chip at one of the at least one sample, whereby the first order beam is incident on the one of the at least one sample from side by an incident angle, so as to generate a fluorescent light if the one of the at least one sample contains a specific component, wherein the bio-chip also reflects the zeroth order beam;

a filter, used to receive and filter the fluorescent light and the zeroth order beam from the bio-chip, so that the fluorescent can pass; and a signal sensor, used to receive the fluorescent light passing the filter, so as to determine whether or not the one of the at least one sample contains the specific component.

2. The apparatus of claim 1, wherein the zeroth order beam reflected from the bio-chip is led to a servo signal sensor, so as to generate a tracking signal and a focusing signal to control a servo system for alignment.

3. The apparatus of claim 1, wherein the light beam has a wavelength about 400 nm–600 nm.

4. The apparatus of claim 1, wherein the HOE unit comprises a circular HOE.

5. The apparatus of claim 4, wherein the circular HOE includes a plurality of concentric strips, of which widths and pitches gradually increase from center to periphery.

6. The apparatus of claim 1, wherein the objective lens has a numerical aperture of about 0.4–0.6.

7. The apparatus of claim 1, wherein the objective lens comprises one selected from a group consisting of a spherical lens and a rod lens.

8. The apparatus of claim 1, wherein the incident angle resulting from the objective lens is a range about 30–50 degrees.

9. The apparatus of claim 1, wherein the filter only allows the fluorescent light to pass.

10. The apparatus of claim 1, wherein the signal sensor comprises an photosignal sensor.

11. The apparatus of claim 1, wherein the fluorescent light and the zeroth order beam from the bio-chip travel back to the beam splitter through the objective lens and then are led to the filter by the beam splitter.

12. A sieving apparatus for a bio-chip, which has at least one sample to be sieved, the apparatus comprising:

a light source to emit a light beam;

a holographic optical element (HOE) unit, used to receive the light beam from the light source and diffract the light beam to form a zeroth order beam and a first order beam, wherein the zeroth order beam remains on an optical path without deflection, and the first order beam is deflected away the optical axis abutting the zeroth order beam;

a first beam splitter, receiving the zeroth order beam and the first order beam from the HOE unit;

an objective lens associating with the first beam splitter, wherein the first beam splitter also leads the zeroth order beam and the first order beam to the objective lens, and the objective lens refracts the zero the order beam and the first order beam to the bio-chip at one of the at least one sample, whereby the first order beam is incident on the one of the at least one sample from side by an incident angle, so as to generate a fluorescent light if the one of the at least one sample contains a specific component, wherein the bio-chip also reflects the zeroth order beam;

a second beam splitter, associated with the first beam splitter to receive the fluorescent light and reflected zeroth order beam and deflect a portion of the zeroth order beam;

a servo signal sensor, receiving the portion of the zeroth order beam deflected by the second beam splitter, so as to generated a tracking signal and a focusing signal to control a servo system, which is used to align the bio-chip for scanning the at least one sample;

a filter, used to receive and filter a rest portion of the fluorescent light and the zeroth order beam from the second beam splitter, so that the fluorescent can pass; and a signal sensor, used to receive the fluorescent light passing the filter, so as to determine whether or not the one of the at least one sample contains the specific component.

13. The apparatus of claim 12, wherein the light beam from the light source has a wavelength of about 400 nm–600 nm.

14. The apparatus of claim 12, wherein the HOE unit comprises a circular HOE.

15. The apparatus of claim 14, wherein the circular HOE includes a plurality of concentric strips, of which widths and pitches gradually increase from center to periphery.

16. The apparatus of claim 12, wherein the objective lens has a numerical aperture of about 0.4–0.6.

17. The apparatus of claim 12, wherein the objective lens comprises one selected from a group consisting of a spherical lens and a rod lens.

18. The apparatus of claim 12, wherein the incident angle resulting from the objective lens is a range about 30–50 degrees.

19. The apparatus of claim 12, wherein the filter only allows the fluorescent light to pass.

20. The apparatus of claim 12, wherein the signal sensor comprises an photosignal sensor.

21. The apparatus of claim 12, wherein the fluorescent light and the zeroth order beam from the bio-chip travel to the second beam splitter through the objective lens, the first beam splitter and then are led to the filter by the second beam splitter.

22. The apparatus of claim 12, wherein the servo signal sensor comprises an optical signal sensor.

* * * * *